_United States Patent_ [19]

De Villiers et al.

[11] 4,090,073

[45] May 16, 1978

[54] DETERMINATION OF MINERAL CONCENTRATIONS IN SLURRIES THEREOF

[75] Inventors: Johan P. R. De Villiers, Johnannesburg; George T. W. Ormrod, Randburgh, both of South Africa

[73] Assignee: National Institute for Metallurgy, Johannesburg, South Africa

[21] Appl. No.: 729,862

[22] Filed: Oct. 5, 1976

[30] Foreign Application Priority Data

Oct. 8, 1975 South Africa ............... 75/6387

[51] Int. Cl.² .................................................. G01N 23/20
[52] U.S. Cl. .................................. 250/273; 250/272; 250/277 R
[58] Field of Search ................... 250/272, 273, 277 R

[56] References Cited

U.S. PATENT DOCUMENTS

| 3,855,470 | 12/1974 | Sahores et al. ............... 250/272 X |
| 3,925,661 | 12/1975 | Carr-Brion ..................... 250/272 |
| 3,980,882 | 9/1976 | Carr-Brion et al. ............ 250/272 |
| 3,982,126 | 9/1976 | Von Alfthan ................... 250/272 |

_Primary Examiner_—Archie R. Brochelt
_Attorney, Agent, or Firm_—Cushman, Darby & Cushman

[57] ABSTRACT

A method of x-ray diffraction determination of the concentration of predetermined minerals in slurries comprises presenting a sample in the form of a stream of slurry having areas of two opposing sides thereof unsupported by any boundary walls therefor, and making required determinations through the unsupported areas of the stream of slurry using x-radiation of a suitable wavelength.

11 Claims, 8 Drawing Figures

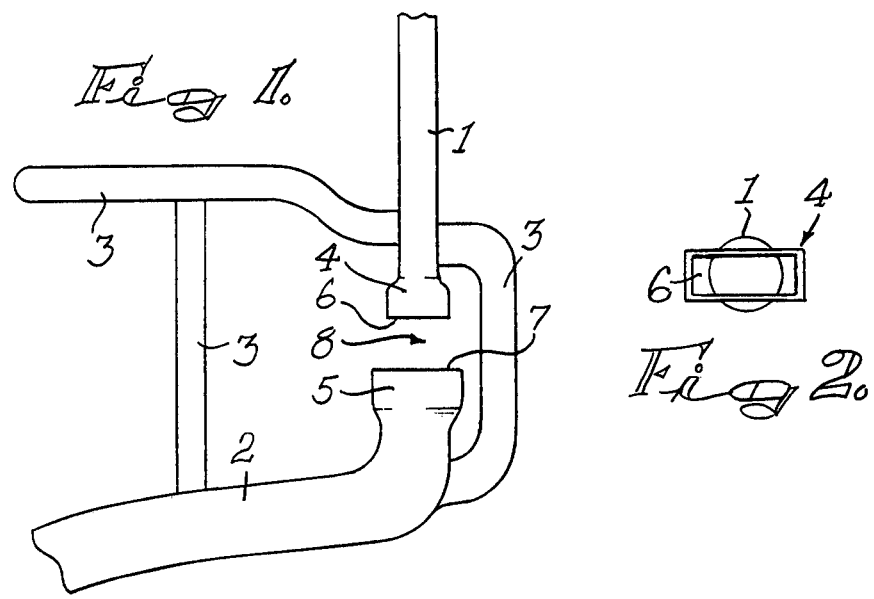
Fig. 1.
Fig. 2.
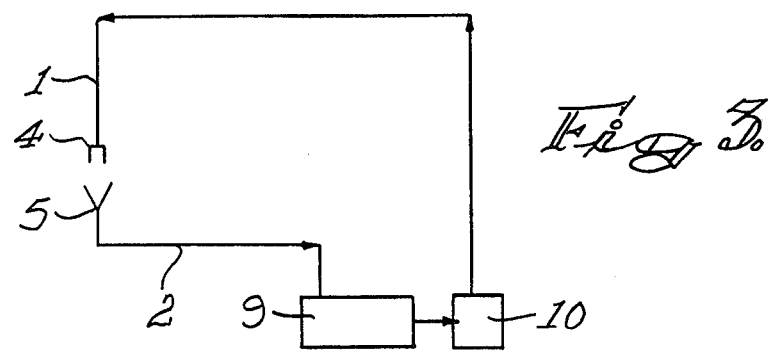
Fig. 3.
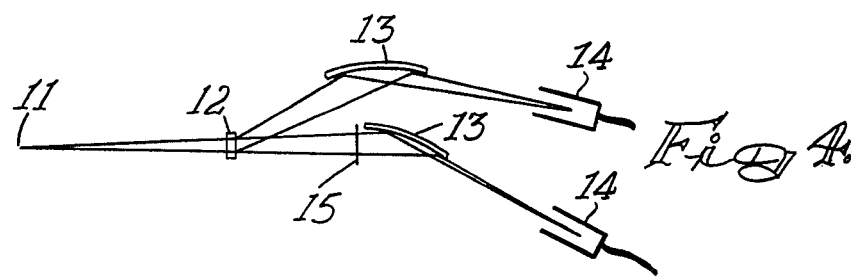
Fig. 4.

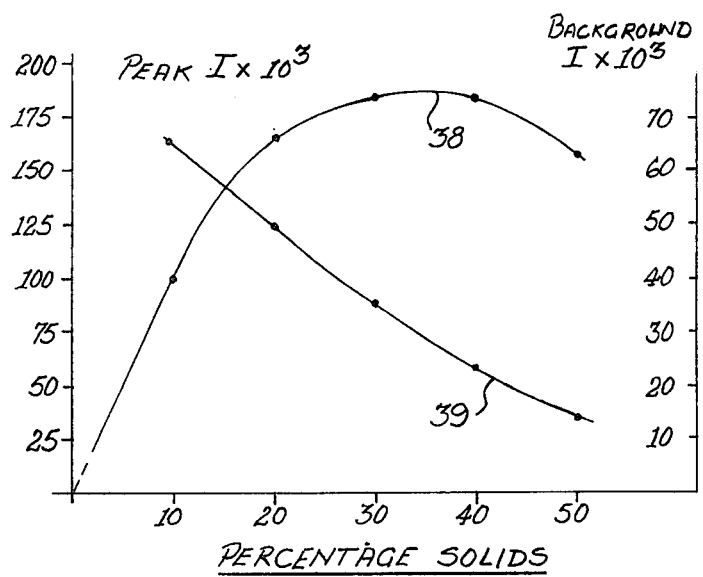
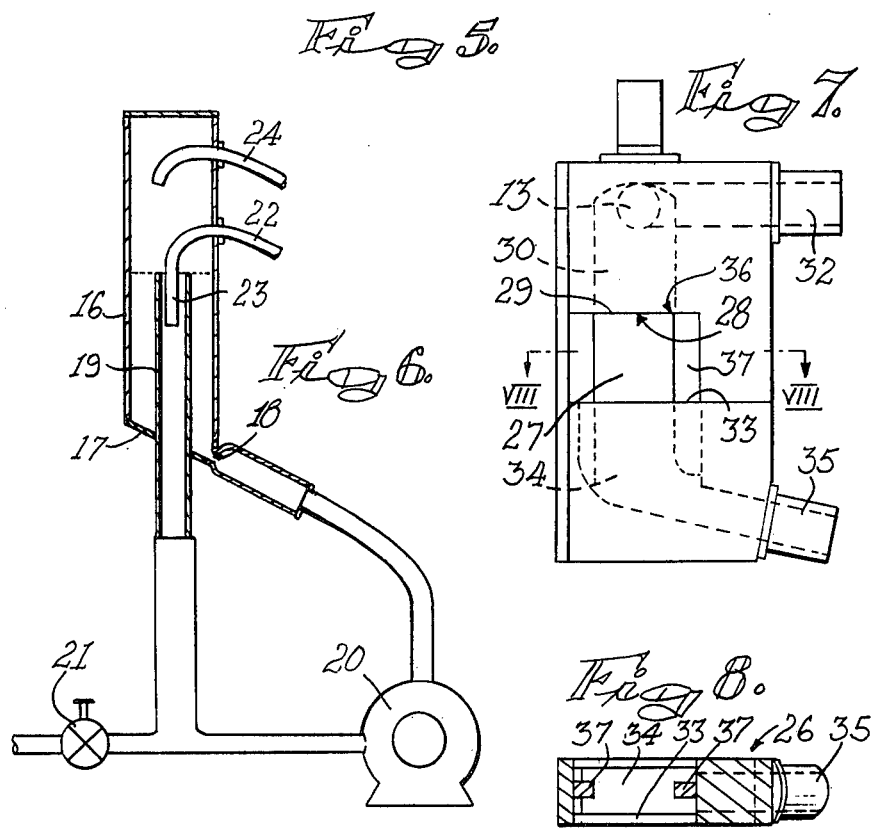

DETERMINATION OF MINERAL CONCENTRATIONS IN SLURRIES THEREOF

This invention relates to the determination of concentrations of minerals in slurries thereof and more particularly the invention is concerned with such determinations which may be carried out on the slurries themselves on a continuous or discontinuous basis.

In the treatment of slurries, for example, the flotation thereof, it is often desirable to have means for determining the concentration of a particular mineral therein for the purposes of process control. Further, laboratory techniques are not generally appropriate in view of the delay in obtaining the required results which are of much greater use if obtained immediately.

To provide rapid analytical results the use of x-ray diffraction in a reflection type of geometry with a flowing slurry sample presented under a mylar window has been proposed. However, the background noise in such a case has to be too great to give sufficiently accurate results. Also if the level of slurry under the mylar window varies, substantial inaccuracies result.

It is an object of this invention to provide an x-ray diffraction method of determining mineral concentrations in slurries thereof wherein a satisfactory signal to background noise ratio is obtained and which can, therefore, be used as a continuous or intermittent control aid.

In accordance with one aspect of the invention there is provided a method for the x-ray diffraction determination of the concentration of predetermined minerals in slurries comprising presenting a sample in the form of a stream of slurry having areas of two opposing sides thereof, unsupported by any boundary walls therefor, and making required determinations through the unsupported areas of the stream of slurry using x-radiation of a suitable wavelength.

Further features of the invention provide for the stream of slurry to be a vertically orientated stream, having two substantially parallel sides; for the determinations to be effected using a transmission geometry for the x-radiation; and for the wavelength of the x-radiation to be shorter than 1,392 A (Angstrom) and in particular for the x-radiation to be MoKα radiation.

The invention also provides a device for presenting a slurry sample in the form of a stream thereof the device comprising a feed tube whereof the outlet is an elongated slot directed towards a receiving formation spaced therefrom; the feed tube being arranged in use to present a stream of slurry the cross-section of which has two substantially parallel sides, the slurry being received in the receiving formation.

Further according to the invention the feed tube is co-axial with the outlet; the end of the elongated slot each have a guide member for the slurry stream directed towards the receiving formation, and the guide members are parallel to each other.

The above and other features of the invention will become more apparent from the following description. In this description the determination of the apatite content of slurries thereof will be discussed but it is to be understood that the invention may be applied to the determination of other mineral concentrations.

In the description reference will be made to the accompanying drawings in which:

FIG. 1 is an elevation of a device for presenting a slurry sample;

FIG. 2 is a plan of the orifice of the feed tube of the device;

FIG. 3 is a simplified slurry flow diagram for the apparatus used;

FIG. 4 is a schematic plan view of the x-ray path used in the apparatus,

FIG. 5 is a graph depicting results given in the description of the invention;

FIG. 6 is a sectional elevation of a slurry circulating apparatus for the device;

FIG. 7 is an elevation of an alternative embodiment of the device; and

FIG. 8 is a section along VII — VIII in FIG. 7.

In this application of the invention a device for presenting a slurry sample (see FIGS. 1, 2 & 3) comprises a feed tube 1 and a return tube 2 secured together by bracing members 3 and each having an end 4 and 5 directed co-axially towards but spaced from each other. The end 4 of the feed tube 1 is formed into an outlet 6 in the form of a rectangular slot, the inside dimensions of which are 9mm by 3mm. This outlet 6 enables a vertical stream of slurry rectangular cross-section to be emitted therefrom.

Opposing the outlet at the end 5 of the return tube is a similarly shaped but larger receiving formation 7 for the slurry. The space 8 between the outlet 6 and receiving formation 7 is sufficiently large to provide a film of slurry of the correct height for use as a sample in x-ray diffraction determination.

As shown in FIG. 3 the device may be connected in series with a sump 9 and a pump 10 for circulating the sample under analysis. Alternatively, the device may be used in an "on stream" mode in a mineral processing plant for example.

It is preferred that transmission geometry be used for the x-ray determination on the slurry sample. Included in the system shown in FIG. 4 is an x-ray source 11, the x-rays of which pass through the slurry sample 12 in the space 8. The diffracted beam passes via a curved quartz monochromator 13 to a scintillation counter 14. In the case of the absorbed beam a tin attenuating foil 15 is placed between the sample 12 and the quartz monochromator crystal 13. The x-radiation used is MoKα radiation.

Two sets of experiments were conducted on slurries using the device described above. Firstly, diffraction patterns of 10, 20, 30, 40 and 50% w/w slurries were determined. Very good signal-to-background ratios were obtained from the more dense slurries. The water created a diffuse scattered background which decreased markedly for the denser slurries.

Table 3 gives the signal-to-background ratios ($N_T/N_B$) theoretical standard deviations ($\delta_o$), root mean square deviations of 10 consecutively measured intensities measured for 100 seconds ($\delta_{rms}$) and detection limits calculated from average apatite contents of 91,8 percent (D), for slurries of different densities using MoKα.

From the results in Table 3 it is clear that radiation in transmission mode gives good sensitivity. It has additional advantages that a very simple sample presentation is necessary, positioning of the sample presenter is not critical at all, and that the primary beam can be measured together with the diffracted beam.

TABLE 3
PEAK-TO-BACKGROUND RATIOS, THEORETICAL AND MEASURED STANDARD DEVIATIONS OF PEAK INTENSITIES AND DETECTION LIMITS IN SLURRIES OF DIFFERENT DENSITIES

| Density slurry | $N_T/N_B$ | $\sigma_c(\%)$ | $\sigma_{rms}(\%)$ | D (% apatite) |
|---|---|---|---|---|
| 10 | 1,39 | 1,77 | 1,93 | 2,7 |
| 20 | 2,33 | 0,68 | 0,60 | 1,1 |
| 30 | 3,57 | 0,44 | 0,72 | 0,68 |
| 40 | 5,47 | 0,34 | 0,29 | 0,33 |
| 50 | 7,84 | 0,29 | 0,30 | 0,33 |

From Table 3 it can be seen that the peaks have extremely low standard deviations of 0.3 percent when compared with a relative error of 2.5 percent in the case of the powder samples. The close correspondence of $\delta_c$ and $\delta_{rms}$ is proof that no additional errors other than those from counting statistics are present. The $\delta_c$ is calculated purely from counting statistics whereas $\delta_{rms}$ represents the observed error in intensity. The detection limits of 0.3 percent apatite are low enough to possibly examine flotation tailings in addition to head samples and concentrates.

A second set of experiments were conducted under the following conditions:

| | |
|---|---|
| Radiation | : MoK$\alpha$ |
| Operating Potential | : 50 kV, 28 mA |
| Counter | : Scintillation counter |
| Voltage | : 740 V |
| Discrimination | : Lower level 1,60 V |
| | Window 2,40 V |
| | Attenuation $2^2$ |
| Goniometer slits | : 2° divergence slit |
| | 0,2 mm - 1° receiving slits |
| Monochromator | : Elastically bent Quartz (1011) |
| Attenuating foil for direct beam | : 0,3 mm Sn situated between sample and monochromator |
| Sample presenter | : Glass with approx. 2 mm outlet |
| Counting interval | : 100 sec. |

The first part of the set of experiments relating to particle size effects was conducted as follows:

A pure apatite sample was ground and screened into four particle size fractions:

−600 + 250μ, −250 + 90μ, −90 + 63μ, −63μ

These were analyzed by x-ray diffraction and the percentage solids kept at a constant weighed value of 40 percent. At the end of each measuring sequence the percentage solids was determined experimentally by drying the suspension collected at the outlet 6 of the feed tube.

The results of the analysis of particle size fractions of apatite are given in Table 4.

TABLE 4
PERCENTAGE SOLIDS AND INTENSITY VALUES FOR SIZED APATITE FRACTIONS

| | Size fraction | Weighed Density | Measured Density | Intensity |
|---|---|---|---|---|
| 1. | −600 + 250μ | 40% | 50,3% (2)* | 139704 |
| 2. | −250 + 90μ | 40% | 35,9% (3) | 178166 |
| 3. | −90 + 63μ | 40% | 39,1% (2) | 182150 |
| 4. | −63μ | 40% | 39,3% (2) | 183613 |

*Figure in brackets denotes the number of measurements.

From Table 4 it is clear that segregation of coarse particles occur in size fractions 1 and 2. This is shown by a variation in slurry densities measured. Only in the last two fractions is the mixing of solid and water adequate. The presence of coarse particles causes a reduction in the measured intensities.

Thereafter the effect of percentage solids in the slurry was investigated using solids in the size fraction −90 + 63μ to minimize the settling effect of the coarse particles. Slurry densities of 10%, 20%, 30%, 40% and 50% by weight of pure apatite were used. Results are indicated in Table 5 and plotted in the graph of FIG. 5. The line denoted by numeral 38 denotes the peak intensity whereas the line denoted by numeral 39 denotes the background intensity.

TABLE 5
VARIATION OF PEAK AND BACKGROUND INTENSITY, WITH SLURRY DENSITY

| Percentage Solids | Peak Intensity | Background Intensity | I/Io |
|---|---|---|---|
| 10% | 100203 | 65239 | 0,620 |
| 20% | 165225 | 49455 | 0,476 |
| 30% | 184411 | 35660 | 0,341 |
| 40% | 184069 | 23120 | 0,221 |
| 50% | 159062 | 13990 | 0,131 |

From FIG. 5 it can be seen that the peak intensity is extremely dependent on the percentage solids and therefore on the increased absorption as shown in the last column of Table 3. This causes a non-linear variation in intensity.

Finally, determinations were carried out on samples from an apatite flotation circuit. The final results are shown in Table 6 which also includes comparative chemical analysis results of the same samples.

From absorption theory the product of the mass absorption coefficient and the thickness $\mu^* t$ can be calculated as follows:

$$I = Io \exp - \mu^* \rho t$$

where
 $I$ attenuated direct beam
 $Io$ original direct beam
 $\mu^*$ mass absorption coefficient
 $\rho$ density (g cm$^{-3}$)
 $t$ thickness of absorber Since I, Io and $\rho$ are measured the product $\mu^* t$ can be calculated.

According to diffraction theory the intensity of a phase $i$ is dependent on the following:

$$I_i = K_i(xi/\mu^*_m \rho_i)$$

where
 $I_i$ intensity of component $i$
 $K_i$ constant of geometry and component $i$
 $\mu^*_m$ mass absorption coefficient of sample
 $\rho_i$ density of component $i$
 $xi$ weight fraction of component $i$.

If a standard of pure component $i$ is used, the amount of component $i$ in a sample can be calculated according to the formula.

$$(I_i/I_s) = x_i(\mu^*_s t/\mu^*_m t)$$

where
 $I_s$ intensity of standard
 $I_i$ intensity of $i$ in sample
 $x_i$ mass fraction of $i$ in sample
 $\mu^*_s t$ absorption product of standard
 $\mu^*_m t$ absorption product of sample.

TABLE 6
APATITE CONTENTS OF FOSKOR SAMPLES

| Sample | Apatite Content (x-ray) | Apatite Content (chemical) |
|---|---|---|
| A | 31% | 35,1% |
| B | 71% | 88,1% |
| C | 87% | 86,7% |

TABLE 6-continued

APATITE CONTENTS OF FOSKOR SAMPLES

| Sample | Apatite Content (x-ray) | Apatite Content (chemical) |
|---|---|---|
| D | 10% | 11,8% |
| E | 17% | 16,2% |
| F | 78% | 95,9% |
| G | 5% | 4,8% |
| H | 21% | 18,8% |
| I | 19% | 17,4% |
| J | 80% | 90,3% |
| K | 8% | 5,3% |
| L | 26% | 24,5% |

The results in table 6 indicate serious discrepancies between the x-ray determination and the chemical determination, especially for samples B, D, F and J. However, it is felt that these discrepancies are basically the result of the inability of the particular instrument used to produce reproducible analyses.

FIG. 6 shows an alternative embodiment of an improved apparatus for feeding the device of the invention. This apparatus comprises an elongated tubular sump 16 having a sloping bottom 17 which terminates at one part of its periphery in an elliptical outlet 18. Projecting centrally through the bottom 17 and extending about halfway into the sump 16 is an inlet tube 19. The inlet tube 19 and the outlet 18 are connected to the corresponding sides of a peristaltic pump 20 which circulates the slurry in the sump. A drain 21 for the sump is provided on the outlet side of the pump.

The sample presenting device is siphonically fed with slurry by a tube 22 which siphons slurry from inside the inlet tube 19 of the sump 16 as shown at 23. After passing through the device the slurry is returned to the sump via a peristaltic pump (not shown) and a tube 24.

Advantages associated with this type of feeding apparatus includes:

(1) A more representative sample fraction. The whole circulating slurry load rapidly passes the inlet of tube 22 deviating only a representative portion of that load to the tube.

(2) A means of de-aerating the slurry. The returned aerated slurry fraction from the device is fed via a pump to the tube 24 into the top of the sump 16 so that air may escape from this returned sample fraction before it rejoins the main slurry circulation.

(3) A means of providing a constant sample fraction flow to the device by use of a steady head. The level of which is at 25.

Since the experimental work described above was done an improved sample presenting device has been developed as shown by FIGS. 7 & 8. This device comprises a body 26, of perspex or other suitable material, having a rectangular window 27 of predetermined size therethrough.

Centrally located in the upper side 28 of the window 27 is an outlet 24 in the form of a rectangular slot. This slot penetrates into the body 26 to form a chamber 30 which is fed by an inlet 31. The inlet feeds into one of the larger sides of the chamber as shown and the inlet tube 32 includes a right angled bend a short distance before the inlet.

In the lower side 33 of the window 27 is a slurry receiving formation 34 which includes an outlet 35 therefor. The cross-sectional area of the formation 34 is considerably larger than the area of the rectangular outlet slot 29 so that spillage of the slurry is minimised.

At each end 36 of the outlet is a flush guide member 37. These guide members are parallel to each and project downwardly into the receiving formation 34. In use the slurry attaches itself to the guide members according to the wall attachment principle.

It has been found that a sample presenting device of this nature has several advantages of the device initially used in the experimentation. These advantages include:

(1) A thinner and more consistent slurry stream may be obtained by use of the side walls, than is obtainable with the shaped outlet of the prior device. This is superior for x-ray analysis.

(2) Manufacturing tolerances are less critical for this device than for a shaped outlet, when repeatability of the liquid stream contours is required.

(3) Clogging by coarse particles is less in this device than for a shaped outlet which by definition must constrict the supply stream.

The above discussion indicates that the method and apparatus of the invention provide a potentially powerful tool in the control of mineralogical processes. It should however be noted that the scope of the invention is not limited by the discussion and that many other applications are envisaged.

What we claim as new and desire to secure by Letters Patent is:

1. A method for the x-ray diffraction determination of the concentration of predetermined minerals in slurries comprising presenting a sample in the form of a stream of slurry having areas of two opposing sides thereof unsupported by any boundary walls therefor, and making required determinations though the unsupported areas of the stream of slurry using the transmitted geometry of the x-ray diffraction technique employing x-radiation of a suitable wavelength.

2. A method as claimed in claim 1 in which the stream of slurry is a vertically orientated stream, having two substantially parallel sides which sides include the unsupported areas.

3. A method as claimed in claim 2 in which the stream of slurry has two opposite sides which are supported, which sides do not include the unsupported areas.

4. A method as claimed in claim 1 in which the x-radiation has a wavelength shorter than 1,392 A (Angstrom).

5. A method as claimed in claim 4 in which the x-radiation is MoKα radiation.

6. A method as claimed in claim 3 in which the supported sides are supported by guide members according to the wall attachment principle.

7. A method as claimed in claim 6 in which control of the physical dimensions of the stream is aided by the guide members.

8. A method as claimed in claim 1 applied in the on-line determination of the concentration of minerals in slurries.

9. A method for the x-ray diffraction determination of the concentration of predetermined minerals in slurries, said method comprising presenting a sample in the form of a stream of slurry having areas of two opposing sides thereof unsupported by any boundry walls therefor, and making required determinations through the unsupported areas of the stream of slurry using the transmitted geometry of the x-ray diffraction technique employing x-radiation of a wavelength shorter than 1, 392 A, said x-ray diffraction method providing an improved signal to background noise ratio.

10. A device for presenting a slurry sample in the form of a stream thereof, the device comprising a feed tube the outlet whereof is an elongated slot directed towards an arranged receiving formation spaced therefrom, each end of the slot having a guide member for the slurry stream directed towards the receiving formation; the feed tube being arranged in use to present the stream of slurry such that in the area between the slot and the receiving formation it has a cross-section having two opposite unsupported sides and two opposite sides supported by the guide members.

11. A device as claimed in claim 10 in which the guide members are parallel to each other.

* * * * *